United States Patent
Murphy

(10) Patent No.: US 8,810,379 B2
(45) Date of Patent: Aug. 19, 2014

(54) BED EXIT NIGHT LIGHT

(76) Inventor: Daniel R. Murphy, Grandview, TX (US)

( * ) Notice: Subject to any disclaimer, the term of this patent is extended or adjusted under 35 U.S.C. 154(b) by 0 days.

(21) Appl. No.: 13/598,568

(22) Filed: Aug. 29, 2012

(65) Prior Publication Data

US 2014/0062342 A1    Mar. 6, 2014

(51) Int. Cl.
*G08B 5/22* (2006.01)
*A61B 5/11* (2006.01)
(52) U.S. Cl.
CPC .................. *A61B 5/1115* (2013.01)
USPC .................. 340/286.07; 340/575
(58) Field of Classification Search
CPC ....................................... A61B 5/1115
USPC ............................ 340/286.07, 575
See application file for complete search history.

(56) References Cited

U.S. PATENT DOCUMENTS

| | | | |
|---|---|---|---|
| 6,049,281 A * | 4/2000 | Osterweil | 340/573.4 |
| 8,081,083 B2 * | 12/2011 | Hinterlong | 340/573.4 |
| 2004/0046668 A1 * | 3/2004 | Smith et al. | 340/573.7 |
| 2004/0257237 A1 * | 12/2004 | Bialecki et al. | 340/686.1 |
| 2006/0049937 A1 * | 3/2006 | Gerder et al. | 340/539.12 |
| 2008/0256445 A1 * | 10/2008 | Olch et al. | 715/700 |
| 2009/0119843 A1 * | 5/2009 | Rodgers et al. | 5/611 |
| 2011/0102181 A1 * | 5/2011 | Metz et al. | 340/575 |
| 2011/0302720 A1 * | 12/2011 | Yakam et al. | 5/710 |
| 2012/0025991 A1 * | 2/2012 | O'Keefe et al. | 340/573.4 |

* cited by examiner

*Primary Examiner* — Jason M Crawford
(74) *Attorney, Agent, or Firm* — Norred Law, PLLC; Warren V. Norred

(57) ABSTRACT

The invention is a Bed Exit Night Light System designed to illuminate a hospital room if a patient leaves his bed, but is not activated by the presence of hospital staff or casual movement of equipment.

2 Claims, 2 Drawing Sheets

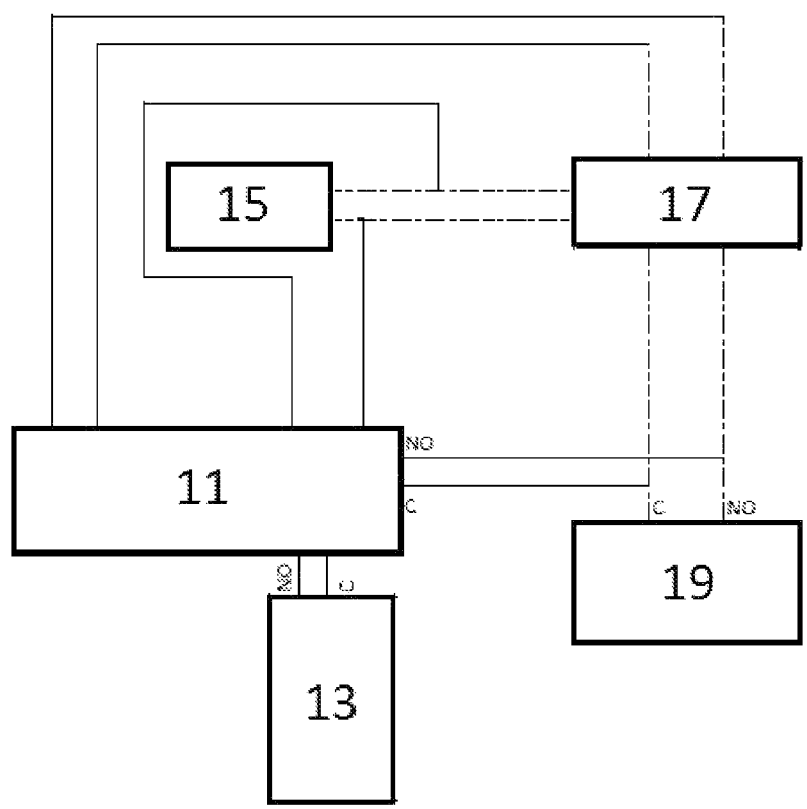

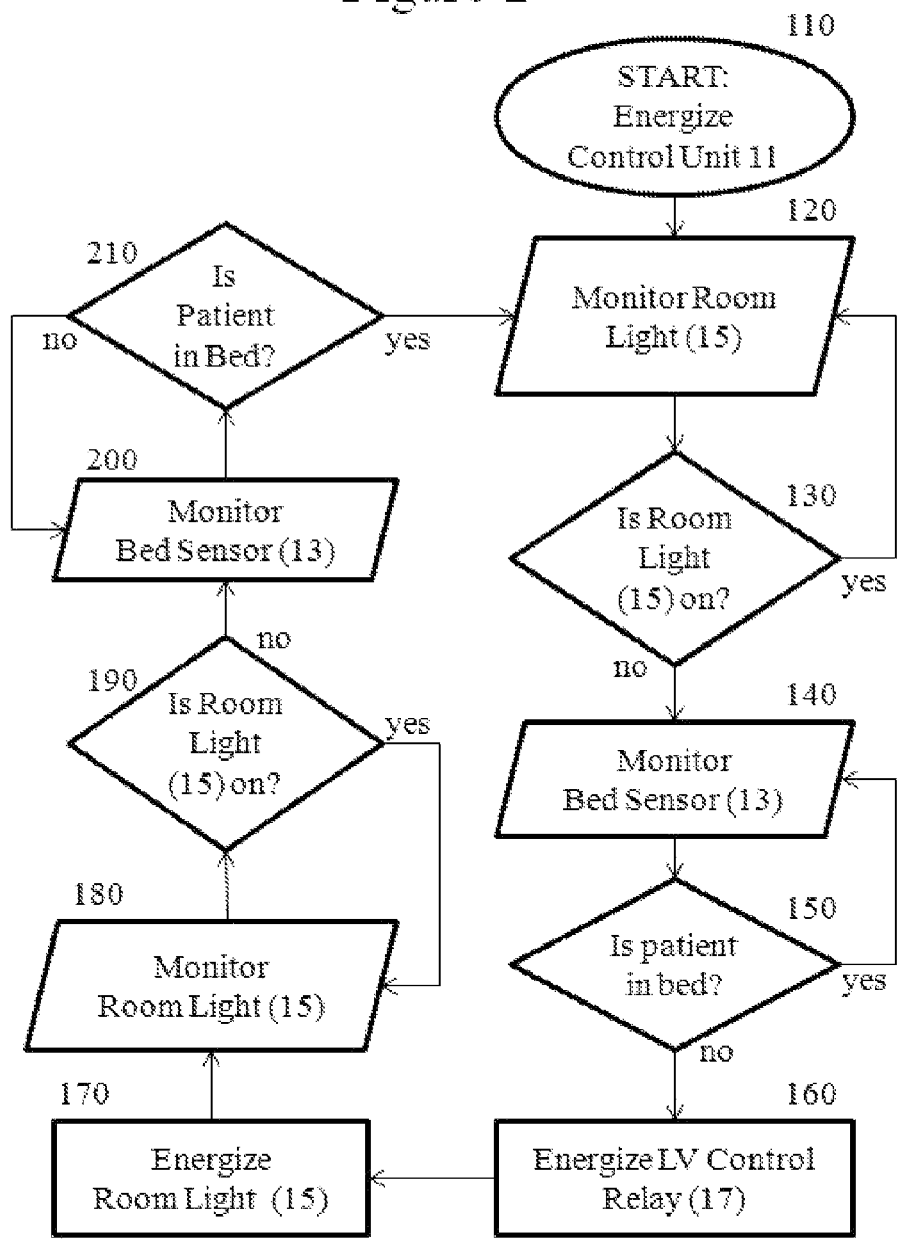

BED EXIT NIGHT LIGHT

CROSS-REFERENCES TO RELATED APPLICATIONS

None.

STATEMENT REGARDING FEDERALLY SPONSORED RESEARCH AND DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

1. Field of the Invention

The invention concerns hospital bedroom lighting.

2. Background Art

Hospitalized patients often struggle when they waken in unfamiliar rooms, and can hurt themselves by attempting to navigate in the dark. The industry has a variety of lighting systems to handle this challenge, none of which provide a satisfactory solution, as follows.

U.S. Pat. No. 6,234,642 discloses a solution in which a lighting system is added to a bed's undercarriage, that illuminates the area around the edge of the bed. The lighting function of this product is designed for use primarily in multi-bed hospital patient rooms, and therefore the light only illuminates the area under the edge of the bed, so as not to disturb other patients in the room.

The dim, narrowly focused light does not illuminate enough of the room to allow the patient to safely navigate their way to and from the restroom at night, which is how and why most patient falls within a hospital occur. Moreover, a hospital must buy the specific bed model that has the lights installed in order to gain the benefit of the light associated with the bed. There is no capability to use this product to retrofit existing beds.

U.S. Pat. No. 5,600,305 discloses a bed-exit sensing system that employs an infrared sensor been that sits low near the bed and parallel to the bedside to detect a patient leaving the bed.

This system has many problems. Modern hospital beds that have integral bed exit-sensing have made this system obsolete. Since a patient could potentially exit the bed from either side, it appears that two of the systems would be necessary, or at least the system would have to be changed from one side to the other.

This system also is duplicative of modern hospital beds, which tend to have an integral patient-detection signal that can be used for any purpose, and makes the signal system irrelevant. And finally, the IR beam will be interrupted as hospital staff move within the room and equipment is moved within the room, as electric cables and signal wires are repositioned. This movement will create false positive signals of patient movement. Movement of equipment will cause the system sensors to require frequent realignment.

The system does have a light that is mounted to the "Master Unit" that, according to the Abstract, sits on the patient floor, but with all of the false alarms that this system is bound to generate, the light would be on almost constantly and if bright enough to be effective, would keep the patient awake.

U.S. Pat. No. 5,471,198—This patent discloses a bed-mountable system that senses the presence or absence of a patient by using a reflected electromagnetic beam. It includes an output relay that "may alternatively operate an alarm bell or light to indicate the absence of the patient". In this case, the implication is that the "light" is intended to be an indicator light to alert staff, similar to the way a nurse call corridor light indicates an active call. It does not, in and of itself, include any kind of lighting to illuminate the patient room.

The ability to detect the presence of a patient in a hospital bed has been perfected by bed manufacturers. This patent is still valid, but irrelevant to today's hospital beds, which routinely come with patient detection systems.

U.S. Pat. No. 4,067,005—This patent discloses a "patient exit" signal, in which pressure sensors are mounted to the bed side rails. The signals are intended to detect when the patient is attempting to exit the bed and "sound a buzzer, and/or a call bell, and/or illuminate the bed so that a nurse or attendant is amply alerted . . . "

Once again, as in above patents and current products, the purpose is to illuminate only the bed itself to alert staff. It is not intended to illuminate the room. Other obvious problems are that the patient may accidently set the system off by grabbing the side rail when they are attempting to simply change their position in the bed; visitor and staff may set it off by leaning over the side rail to tend to the patient or lower it. Multiple false alarms tend to cause the staff to ignore all alarms.

These patents summarize the prior art, which focuses on ways of detecting the presence of patients in beds, a task easily handled by modern hospital beds. The hospital bed industry needs a system that will assist hospitalized patients by lighting rooms only when patients leave their beds, does not light the room unduly by activating without false positives and does not create a need for hospital staff to modify their everyday operations to maintain the system.

BRIEF SUMMARY OF THE INVENTION

The invention shown in FIG. 1 is a Bed Exit Night Light System designed to illuminate a hospital room if a patient leaves his bed, but is not activated by the presence of hospital staff or casual movement of equipment.

The system is based on a Control Unit 11 that monitors the Bed Sensor 13 when the Room Light 15 is off, energizing the Room Light 15 when a patient leaves the bed, and keeping the Room Light 15 on until deactivated by the patient or hospital staff.

BRIEF DESCRIPTION OF THE SEVERAL VIEWS OF THE DRAWING(S)

FIG. 1 is a block diagram of the invention.
FIG. 2 is a flow chart for the invention's operation.

DETAILED DESCRIPTION OF THE INVENTION

The invention described herein builds upon existing components of modern hospital beds, adding a Control Unit 11 that is only active when a patient's room lighting is not operating, but turns the Room Light 15 on when the room's lighting is off and a patient gets out of bed. In an alternate configuration, the invention only functions when the room is dark. In practice, the invention comprises the Control Unit 11 and new wiring connections that employ an existing bed sensor, but retro-fit kits may also include the Bed Sensor 13, Low Voltage Light Control Relay 17, Light Control Button 19, and associated wiring.

FIG. 1 shows a control diagram showing the physical connection between the various components of the invention. This diagram assumes that the Low Voltage Control Relay (LVCR) 17 changes state each time its inputs show a closed contact, just as the Light Control Button 19 momentarily closes its normally open contacts to change the state of the LVCR 17. The dotted lines indicate connections that already exist in typical circumstances.

The embodiment shown in FIG. 1 assumes that the Control Unit 11 senses the Room Light 15 operation by monitoring the voltage source across the Room Light 15. Alternatively, the Control Unit could have a light detector which eliminates that direct wired connection.

As shown in FIG. 2, the operation begins when a user activates the system, usually by a button on the Control Unit 11 (Step 110). After activation, the Control Unit 11 begins to monitor the room's overhead light (Step 120). The Control Unit does nothing unless the Room Light 15 is off (Step 130).

When the Room Light 15 is off, the Control Unit 11 monitors the Bed Sensor 13 to determine if a patient is present (Step 140). The Bed Sensor 13 is usually a "normally open" (NO) contact that closes when a patient leaves the bed; this apparatus is included in most modern hospital beds. When a patient leaves the bed, the Bed Sensor 13 changes state, informing the Control Unit 11 of the patient's activity. (Step 150).

The Control Unit can also function with a Bed Sensor 13 that is a "normally closed" (NC) contact here as well; the invention just needs to take into account the status of the contact when a patient is in the bed, and that the status changes when a patient leaves the bed.

When the Control Unit 11 is informed by the Bed Sensor 13 that a patient has left the monitored hospital bed, the Control Unit 11 activates the Low-Voltage Control Relay (LVCR) 17 that most modern hospitals use to operate the Room Light 15 (Step 160).

When activated, the LVCR 17 energizes the Room Light 15 (Step 170). The Control Unit 11 ceases activity while monitoring Room Light 15 (Step 180). The Control Unit 11 monitors the Room Light 15 until de-energized by an outside actor (Step 190).

The Control Unit 11 then monitors the Bed Sensor 13 (Step 200). Once the Room Light 15 is off, and the patient is back in bed, the Control Unit 11 repeats the cycle (Step 210). Alternatively, a timer can also be employed to give a patient time to settle himself before beginning to monitor movement of the patient and avoid false positives.

In the current incarnation, no part of the invention turns the light off, though this could be an added feature. None of the apparatus discussed or shown interferes with the existing light control. The Control Unit 11 triggers the LVCR 17 by emulating the Light Control Button 19 by sending it a closed contact to its inputs.

The point of the flow chart is that the Control Unit 11 turns the Room Light 15 on when a patient gets out of his bed and the Room Light 15 is off, and remains on until the patient or nursing staff turns the light back off. Once the Room Light 15 is on, the Control Unit 11 ignores further input until a patient or one of the hospital staff deactivates the Room Light 15 by using Light Control 19, typically a momentary switch to turn the Room Light 15 off. Then the Control Unit 11 waits until the patient is back in bed and the light is off before starting the monitoring cycle anew.

When the existing Room Light 15 illuminates the room, the patient is brought to a more awakened state when they try to exit the bed and they are able to see all of the potential tripping obstacles in their path, thereby reducing the likelihood of a patient fall.

In typical use, the Control Unit 11 is a permanently-mounted device that is located above the ceiling, but could be mounted anywhere on the patient room head wall, under the bed, or any other out-of-the-way location. Unlike previous solutions to this challenging situation, it is not disturbed by staff or equipment as it is moved around in the patient's room.

Since modern patient beds can sense the patient's weight and only trigger the bed exit alert when the patient's weight is lifted, false alarms are kept to a minimum.

The Invention 11 also has a contact closure output that could then be used to trigger the nurse call system or bed-exit alarm.

The invention claimed is:

1. A Bed-Exit Lighting System, comprising:
 a. a sensor that provides a signal to a control unit when a user leaves a bed;
 b. a room light in the same room as the bed;
 c. a means other than a photoelectric cell for detecting light in the vicinity of the bed which is connected to a control unit;
 d. a relay between the room light and a power source to the room light that connects the power source to the room light upon receiving a control signal;
 e. a control unit connected to the relay, that controls the relay so as to provide power to a room light when a user in the bed gets out of the bed when the room is dark; and
 f. the control unit delays the monitoring of the bed sensor after the room light is turned off for a period of time, allowing a user to get into the monitored bed.

2. A method of controlling room lighting a room with a bed, comprising:
 a. monitoring the room light around a target bed until the room is dark; and,
 b. monitoring a bed sensor that indicates the presence of a person in the bed; and,
 c. energizing a control relay to provide power to the room light when the bed sensor detects that a person is leaving the bed and the room is dark; and,
 d. ceasing operation once the room light is on, until the room light is independently turned off by an outside actor; and then,
 e. waiting a period of time before beginning to monitor the bed sensor after the light is turned off by the outside actor; and then,
 f. repeating this cycle.

* * * * *